United States Patent [19]

Doan

[11] Patent Number: 5,356,378
[45] Date of Patent: Oct. 18, 1994

[54] FLUID LINE CONDITION DETECTION

[75] Inventor: David B. Doan, San Diego, Calif.

[73] Assignee: IVAC Corporation, San Diego, Calif.

[21] Appl. No.: 185,278

[22] Filed: Jan. 24, 1994

Related U.S. Application Data

[63] Continuation of Ser. No. 823,863, Jan. 22, 1992, abandoned.

[51] Int. Cl.$^5$ .............................................. A61M 5/00
[52] U.S. Cl. ..................................... 604/65; 604/153; 128/DIG. 13
[58] Field of Search ..................... 604/65–67, 604/123, 153; 128/DIG. 12, DIG. 13; 417/474

[56] References Cited

U.S. PATENT DOCUMENTS

| | | | |
|---|---|---|---|
| 4,277,226 | 7/1981 | Archibald | 128/DIG. 12 |
| 4,460,355 | 7/1984 | Layman | 604/118 |
| 4,530,696 | 7/1985 | Bisera et al. | 604/253 |
| 4,534,756 | 8/1985 | Nelson | 604/50 |
| 4,617,014 | 10/1986 | Cannon et al. | 128/DIG. 12 |
| 4,710,163 | 12/1987 | Butterfield | 604/67 |
| 4,731,057 | 3/1988 | Tanaka et al. | 604/67 |
| 4,743,228 | 5/1988 | Butterfield | 604/50 |
| 4,836,752 | 6/1989 | Burkett | 604/153 |
| 4,846,792 | 7/1989 | Bobo, Jr. et al. | 604/50 |
| 4,898,576 | 2/1990 | Philip | 604/65 |
| 4,959,050 | 9/1990 | Bobo, Jr. | 604/49 |
| 5,078,682 | 1/1992 | Miki et al. | 604/67 |
| 5,087,245 | 2/1992 | Doan | 604/67 |
| 5,096,385 | 3/1992 | Georgi et al. | 604/67 |
| 5,098,380 | 3/1992 | Aizawa et al. | 128/DIG. 13 |
| 5,103,211 | 4/1992 | Daoud et al. | 604/67 |
| 5,116,203 | 5/1992 | Natwick et al. | 417/474 |

OTHER PUBLICATIONS

Mott, *Applied Fluid Mechanics*, Charles E. Merril Pub. Co., Ohio ©1972, pp. 136–163.

*Primary Examiner*—Ralph A. Lewis
*Attorney, Agent, or Firm*—Fulwider, Patton, Lee & Utecht

[57] ABSTRACT

A compliant chamber is formed in a fluid line which connects a fluid supply to a fluid receiver. The compliant chamber is alternately in fluid communication with the upstream and downstream segments of the fluid line. When the chamber communicates with the upstream segment it receives and stores fluid at the head pressure. When the segment communicates with the downstream segment, a pressure equalization pulse occurs. A pressure sensor in the downstream segment measures the pressure equalization pulse which is proportional to the head pressure. Processing the equalization pulse with the downstream fluid system resistance, the compliance of the compliant chamber and the equilibrium pressure results in a determination of the head pressure. Comparing the head pressure to thresholds permits determination of an occlusion or empty fluid supply. Where a peristaltic pump is used, the chamber is formed between the end fingers of the pump.

35 Claims, 3 Drawing Sheets

FLUID LINE CONDITION DETECTION

This is a continuation of application Ser. No. 07/823,863 filed Jan. 22, 1992 now abandoned.

BACKGROUND

The invention relates generally to monitoring fluid flow, and more particularly, to detecting fluid line conditions upstream of the monitoring position.

Fluid delivery systems having positive pressure pumps for infusing parenteral fluid to a patient have become fairly common. In many cases the pump is a peristaltic type in which a plurality of fingers, rollers, or other devices, sequentially constrict a flexible tube through which the parenteral fluid is supplied. Such fluid delivery systems also include, in addition to the pump, an inverted bottle or bag or other means of supply of parenteral fluid, an intravenous (IV) administration set which is secured to the supply of parenteral fluid and includes the flexible tube, and a cannula which is mounted to the distal end of the tube and which is adapted to be inserted into the patient's blood vessel to thereby infuse the parenteral fluid.

One common problem facing infusion systems is the evaluation of the condition of the fluid supply system upstream of the pump. Where an occlusion of the tube exists upstream of the pump, the pump will not succeed in infusing the parenteral fluid to the patient even though the pump may continue to operate. Where the parenteral fluid supply becomes depleted, once again the pump may continue to operate but no parenteral fluid will be delivered to the patient.

A prior method for detecting depletion of the fluid supply or an upstream occlusion was visual observation. A drip chamber may be inserted in the fluid line at a position downstream from the fluid supply for monitoring the rate and quantity of fluid administered. However, visually verifying the existence of drops requires the time of an attendant which can be an undesirable burden on the hospital staff. Opto-electric drop detectors may be utilized in conjunction with the drip chamber. These detectors are capable of automatically detecting upstream occlusions due to a clamp or kink in the upstream tubing and an empty IV fluid supply container by detecting an absence of drops. An upstream occlusion can also be detected by the addition of a pressure sensor to the fluid line upstream of the pump. However, the use of these devices can add a considerable additional expense. Additionally, movement of the administration set, if severe enough, can cause extra drops to fall from the drop former or can interrupt the drops causing false counts and false alarms. Ambient light can also interfere with an optical drop sensor and render it inaccurate.

In some cases it would be useful to automatically provide information relating to the pressure of the supply fluid or the "head" pressure. From the head pressure, an upstream occlusion can be detected as well as an empty fluid supply.

Pump systems have been disclosed which include a downstream pressure sensor used for detecting improper fluid communication with the patient. Such systems include U.S. Pat. No. 4,743,228 to Butterfield; U.S. Pat. No. 4,460,355 to Layman; U.S. Pat. No. 4,534,756 to Nelson; and U.S. Pat. No. 4,846,792 to Bobo, Jr. et al. Where such systems use a pump or other fluid pressure control means which communicates the head pressure to the outlet side of the pump, it would be of value to utilize the existing downstream pressure sensor to determine upstream fluid conditions. This would result in less expense both in the pump and in the administration sets.

Hence, those skilled in the art have recognized the need for a fluid line monitoring system which can automatically detect upstream fluid line occlusions as well as measure the head pressure. Additionally, those skilled in the art have recognized a need to reduce the cost of determining such upstream fluid line conditions. The present invention fulfills these needs.

SUMMARY OF THE INVENTION

Briefly and in general terms, a fluid chamber is disposed such that it is in fluid communication with an upstream fluid line connected to a fluid supply and a downstream fluid line connected to a fluid receiver, such as a patient. A means, such as a peristaltic pump, is used to alternately expose the fluid chamber to the upstream pressure, or "head" pressure and the downstream pressure. The pressure in the downstream fluid line is sensed to monitor the equilibrium pressure and the pressure equalization pulse caused by exposing the fluid chamber having fluid at the head pressure to the downstream pressure. By monitoring the equilibrium pressure and the equalization pulse and comparing the two, the head pressure can be determined.

In a particular embodiment, a fluid pressure control means, such as a peristaltic pump, establishes a compliant fluid chamber in a fluid line connecting a fluid supply with a patient. The fluid pressure control means alternately exposes the compliant chamber to the upstream segment of the fluid line, during which time the chamber receives and stores fluid at head pressure, and then exposes the compliant chamber to the downstream segment of the fluid line. When exposed to the downstream segment of the fluid line, the fluid at head pressure stored in the compliant chamber communicates with the fluid in the downstream segment and a pressure equalization pulse occurs.

A pressure sensor located in the downstream segment provides a pressure signal representative of the pressure equalization pulse. This pressure equalization pulse is processed to determine upstream fluid conditions. Because this fluid stored in the compliant chamber is at head pressure, the equalization pulse is proportional to the pressure differential between the head and the downstream pressures. The pressure due to the equalization pulse is processed along with the resistance of the downstream system, the compliance of the compliant chamber and the equilibrium pressure to determine the head pressure. From the head pressure, an upstream occlusion and an empty fluid supply can be detected.

In the case of an upstream occlusion, the pump will produce a large negative pressure; i.e., below atmospheric, very quickly. This results in a large negative equalization pulse at the pressure transducer which is readily identifiable. In the case of detecting an empty supply, the head pressure is compared to a threshold and if the pressure is less than that threshold, an alarm is generated.

Detecting an empty fluid supply may also be accomplished by comparing successively measured head pressures and if the change between them exceeds a threshold, an alarm is generated. A relatively rapid change in head pressure may indicate that the supply fluid is down to the narrow part of the drip chamber.

In another aspect, a float valve or a hydrophilic filter or some similar mechanism which will not pass air may be incorporated into the drip chamber or some other portion of the IV set so that when the fluid supply becomes empty, the line will automatically become occluded. The upstream occlusion detection feature may then be used to also indicate an empty fluid supply.

Other aspects and advantages of the invention will become apparent from the following detailed description and accompanying drawings, illustrating by way of example the features of the invention.

DETAILED DESCRIPTION OF THE PREFERRED EMBODIMENTS

Figure 1:
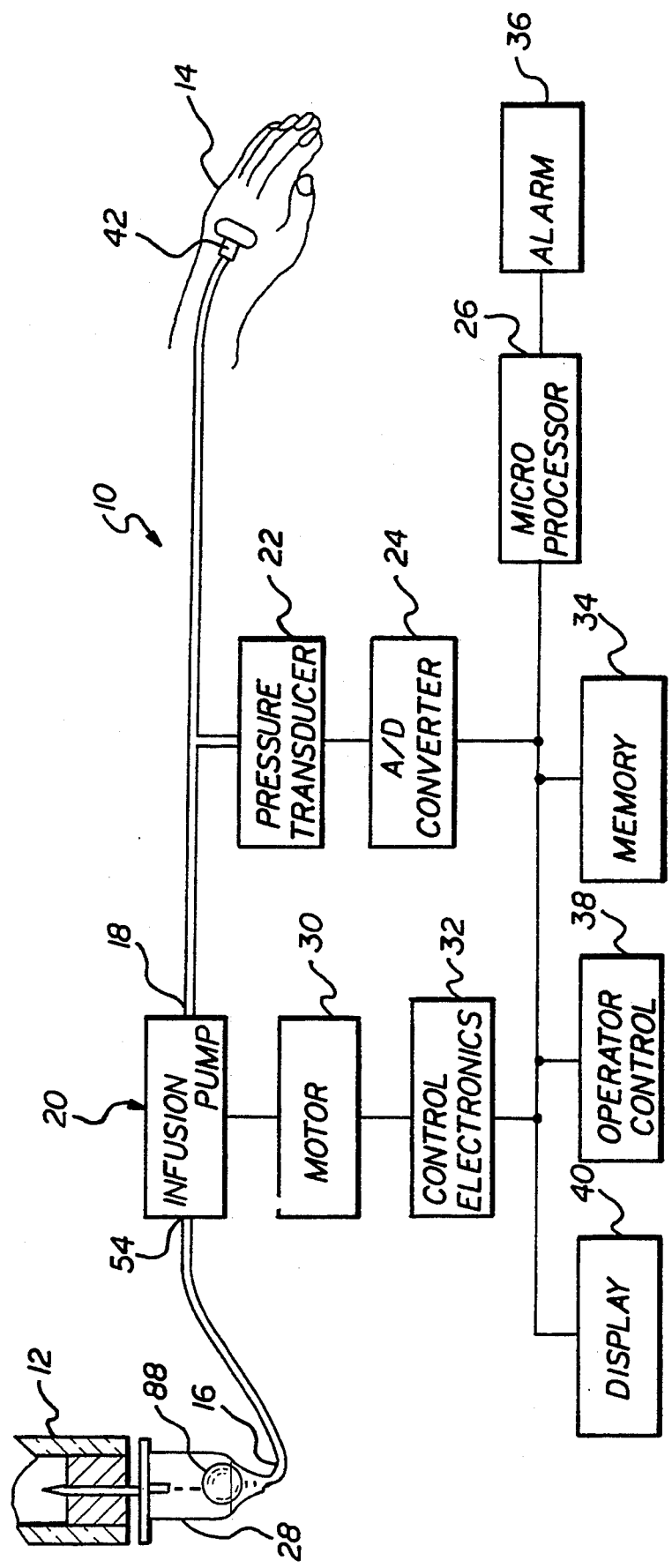
FIG. 1 is a block diagram of an apparatus for detecting conditions in an upstream fluid line incorporating the principles of the invention as applied to an intravascular fluid infusion system.

Referring now to the drawings with more particularity, wherein like reference numerals designate like or corresponding elements among the several views, there is shown in FIG. 1 a system 10 for detecting conditions in a fluid line upstream of a monitoring position. A fluid line, which may be an administration set formed of flexible tubing, is positioned between a fluid supply 12 and a patient 14 and comprises an upstream segment 16, a downstream segment 18 and a pumping segment 44 (shown in FIGS. 2A, 2B and 2C). In this case, the fluid supply comprises an inverted bottle. The pumping segment 44 is operated on by a pressure control means which comprises in this embodiment, an infusion pump 20 to form a compliant chamber as will be described in more detail below. A pressure transducer 22 is coupled to the downstream fluid line segment 18 to sense the pressure in that segment 18 and provide a signal representative of that sensed pressure. An analog-to-digital converter 24 is coupled to the pressure transducer 22 to provide a digital signal to a signal processor 26 shown in this case as a microprocessor which is part of the pump assembly apparatus.

Figure 2:
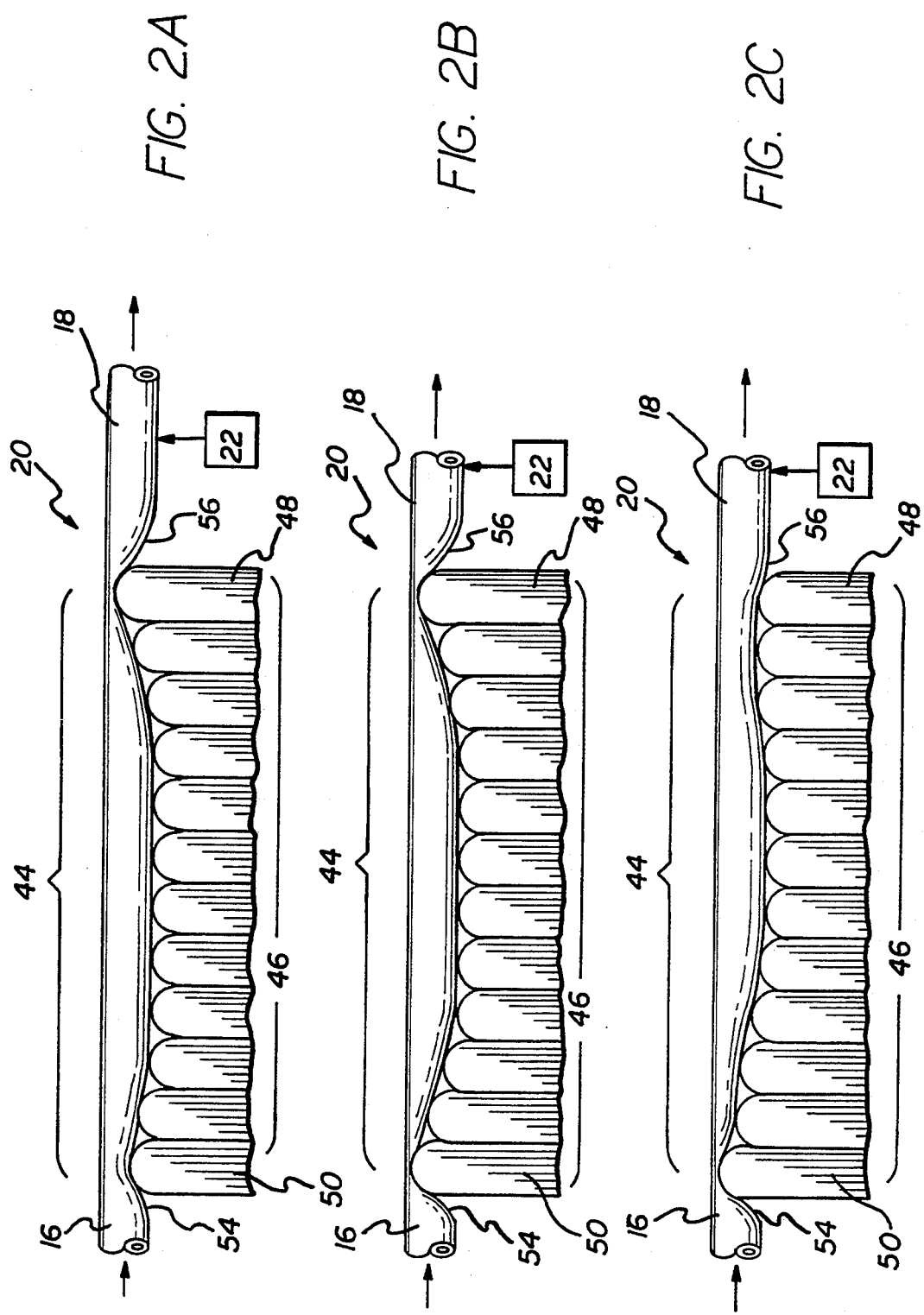
FIGS. 2A, 2B and 2C are diagrams of the operation of a linear peristaltic pump on a segment of compliant tubing showing in particular the establishment of a compliant fluid chamber.

In FIG. 1, the upstream fluid line segment 16 is connected to the supply bottle 12 through a drip chamber 28 in this embodiment. The upstream segment 16 supplies fluid to the infusion pump 20 which in the embodiment of FIGS. 1 and 2 is a linear peristaltic pump. The pressure of the fluid at the pump inlet 54 will be the "head" pressure. A motor 30 and control electronics 32 are used to drive the peristaltic fingers of the linear peristaltic pump 20. The pump system in this embodiment further comprises the microprocessor 26, a memory 34, an alarm 36, an operator control panel 38 and a display 40. The display unit 40 may comprise a monitor or strip-chart recorder for displaying the head pressure as determined by the microprocessor 26. Mounted at the distal end of the downstream fluid line segment 18 is a cannula 42 used to connect the downstream fluid line segment 18 to the vascular system of the patient 14. The pump 20 supplies the parenteral fluid to the patient 14 at a selected rate and pressure which may be different from the head pressure.

In some prior systems, the output signal from the pressure transducer 22 is processed to detect the existence of a downstream occlusion, infiltration or other condition. Some of these systems are mentioned in the preceding Background section. Thus, a pressure transducer 22 which will supply a pressure signal is already installed in some pump systems.

A typical linear peristaltic pump operates by sequentially pressing on a segment of flexible tubing by means of cam-following fingers. The pressure is applied in sequential locations of the tubing, beginning at the inlet end of the pump and working toward the outlet end. At least one finger is always pressing hard enough to occlude the tubing. As a practical matter, one finger does not retract from occluding the tubing until the next one has already occluded the tubing; thus, at no time is there a direct fluid path from the inlet to the outlet of the pump.

Referring now to FIGS. 2A and 2B, the operation of a linear peristaltic pump 20 in forming a head pressure compliant chamber is shown. The peristaltic pump fingers indicated collectively by numeral 46 create a moving zone of occlusion throughout the length of a pumping segment 44. In FIG. 2A, the most downstream part of the pumping segment or pump outlet 56 is occluded by peristaltic finger 48 while the most upstream peristaltic finger 50 has not yet occluded the pumping segment 44 at the pump inlet 54. Thus, fluid at head pressure is flowing into the pumping segment 44 from the upstream segment 16 but is prevented from communicating with the fluid in the downstream segment 18 by the occlusion caused by the most downstream peristaltic finger 48. Therefore, the pumping segment 44 is now at head pressure.

In FIG. 2B, formation of the compliant chamber 44 is shown. As discussed above, a second finger occludes before an occluding first finger retracts thereby preventing a direct fluid flow between the supply and the patient. In this case, the upstream finger 50 occludes before the downstream finger 48 retracts and there exists a point in time when both fingers 48 and 50 occlude as is shown in FIG. 2b thereby forming the compliant chamber 44 which traps fluid at head pressure.

In FIG. 2C, the most upstream peristaltic finger 50 continues to occlude the pumping segment 44 prior to the most downstream finger 48 retracting from an occluding position. The fluid at head pressure which was trapped in the compliant chamber 44 is now free to communicate with the fluid in the downstream fluid line segment 18. Thus, the compliant chamber 44 is alternately in fluid communication with the upstream segment 16 and the downstream segment 18 of the fluid line.

When the most downstream peristaltic finger 48 retracts thereby allowing fluid communication with the compliant chamber 44, the most upstream peristaltic finger 50 has already occluded the fluid line, thus a bolus of fluid at head pressure, the bolus being the quantity stored in the compliant chamber 44, is released into the downstream segment 18 of the fluid line. Upon its release, the pressure in the compliant chamber 44 and the pressure in the downstream fluid line segment 18 will equalize. A measurable pressure equalization pulse is produced which will be sensed by the pressure transducer 22. This pulse is proportional to the difference between the head and the downstream pressures, and may be processed to determine the head pressure in accordance with the invention.

The flexible material forming the compliant chamber 44 has some compliance ($C_{pump}$) which is taken into account in one embodiment when determining head pressure. It has been found that the compliance is for all practical purposes a property of the tubing because IV fluids are virtually incompressible. When the pressure is changed from $P_1$ to $P_2$, a quantity of fluid "Q" will flow but the quantity is dependent on the tubing compliance as follows:

$$Q = C_{pump}(P_2 - P_1) \qquad \text{eq. 1}$$

If $P_2$ is greater than $P_1$, flow will occur in a forward direction and if $P_1$ is greater than $P_2$, flow will occur in a backward direction. As used herein, "compliance" refers to a measure of elasticity of the material forming the compliant chamber. It is given here as a constant.

The quantity of fluid Q which will flow is also affected by the resistance R of the fluid system in accordance with the following:

$$Q = \frac{1}{R} \int_0^t (P(t) - P_{eq}) dt \qquad \text{eq. 2}$$

where:
R is the total resistance to fluid flow;
P(t) is dynamic pressure; and
$P_{eq}$ is equilibrium pressure
Substituting $P_{head}$ for $P_2$ and $P_{eq}$ for $P_1$ in equation 1 and combining equations 1 and 2 yields:

$$P_{head} = P_{eq} + \frac{1}{RC_{pump}} \int_0^t (P(t) - P_{eq}) dt \qquad \text{eq. 3}$$

where:
$P_{head}$ is the head pressure; and
$C_{pump}$ is the effective compliance of the compliant chamber 44.

As shown in equation 3 above, equilibrium pressure $P_{eq}$ and resistance R are also considered when determining the head pressure. Although determination of equilibrium pressure may be based upon a measurement of pressure in the system before perturbation of the fluid flow by the bolus of fluid at head pressure, equilibrium pressure is preferably averaged over a number of pressure readings both before and after the measurement of the pressure response to the bolus. It is not necessary that the equilibrium state be a state of zero flow. The equilibrium pressure is rather a dynamic one, which is monitored and determined periodically. It is only necessary for the fluid system to be in equilibrium prior to release of the head pressure bolus, and the pressure response can be integrated until it again returns to equilibrium. The baseline or equilibrium pressure $P_{eq}$ is thus average pressure (including that due to flow) in the equilibrium state.

The total fluid flow resistance R is preferably determined by the means disclosed in U.S. Pat. No. 5,087,245 to Doan filed Mar. 13, 1989 incorporated herein by reference, or by the technique disclosed in U.S. Pat. No. 4,743,228 to Butterfield.

The accuracy of this method of determining head pressure depends on the stability of the compliance of the pumping segment 44 from set to set and over time. For use as an occlusion detector, however, great accuracy is not important. If the line is occluded, the pump will produce a large negative pressure; i.e., less than atmospheric very quickly. This results in a large negative equalization pulse at the pressure transducer 22 which is readily identifiable. However, for use as an empty supply detector, a greater degree of accuracy is needed. The supply would be assumed to be empty if the fluid head pressure fell below a specified minimum pressure threshold, or if the head pressure began to change rapidly as it would if the level of the supply fluid were down in the narrow part of the drip chamber, or in the tubing itself.

Further associated with the microprocessor 26 and operator control 28 is an alarm generator 36 responsive to comparisons of the head pressure with one or more reference values or thresholds which are stored in the system memory 34. Reference values may also be input into the memory 34 at the operator control 38 or may be preprogrammed.

Figure 3:
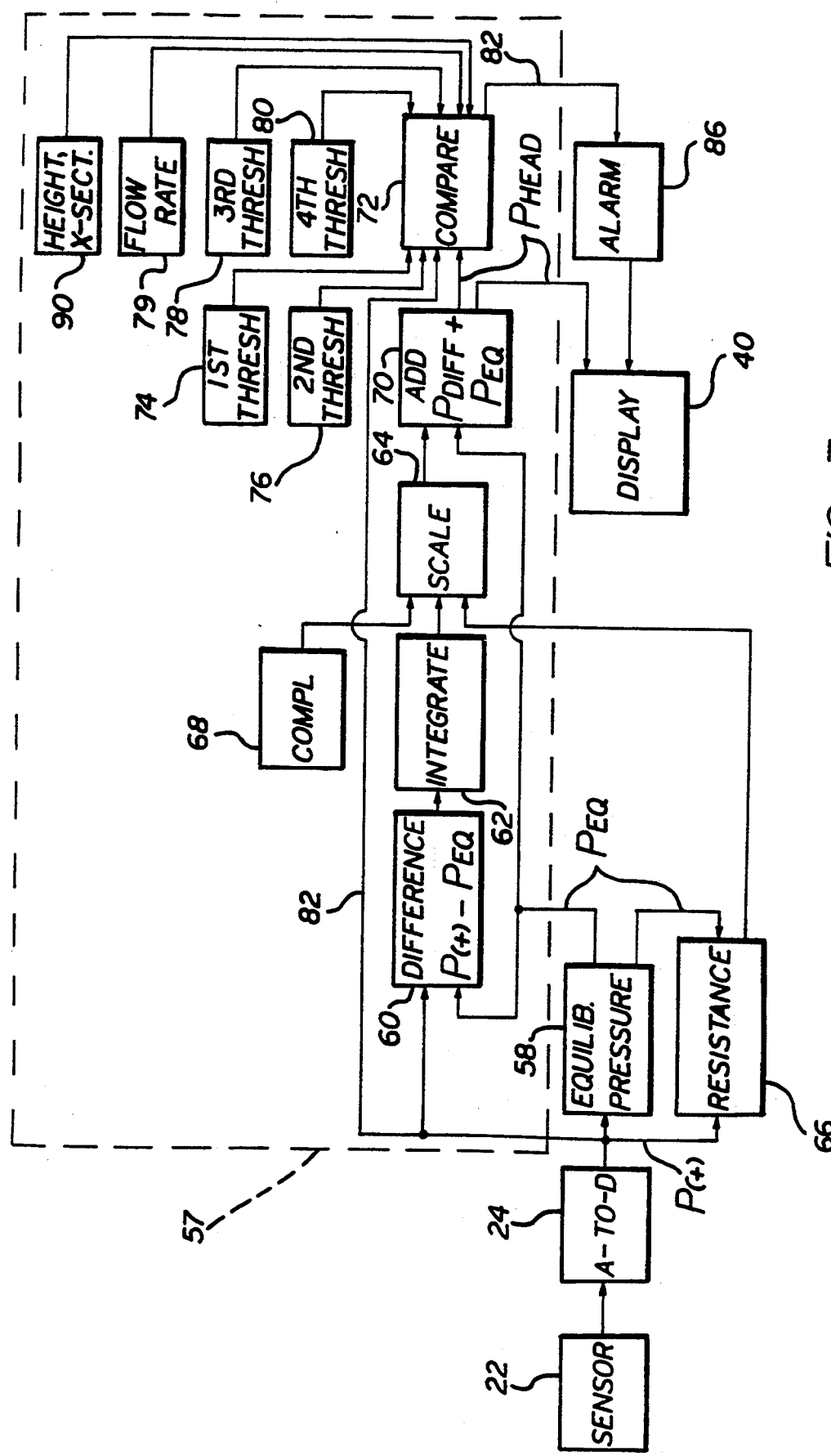
FIG. 3 is a block diagram of a signal processing embodiment for determining head pressure in accordance with the invention.

Referring now to FIG. 3, a processing system 57 in accordance with the principles of the invention for determining head pressure is shown. It is preferable to use as the equilibrium pressure $P_{eq}$ the average of determinations of pressure before and after the release of the head pressure bolus by the compliant chamber 44. This provides considerable immunity from artifacts such as pressure changes due to patient motion. It should be noted that repeated sampling of downstream pressure is intended to be timed so that samples can be equally spaced in time, at intervals of 0.005 seconds for example.

The equilibrium pressure 58 is determined as described above. A series of dynamic pressure samplings are taken, to be compared with the equilibrium pressure 58 as $P(t) - P_{eq}$ in the comparator 60. An integrator 62 for calculating the difference over time is adapted to generate a signal representing the integral. This integral signal is received and scaled in the scaler section 64 according to the fluid flow resistance 66 in the infusion system and the compliance 68 of the material forming the compliant chamber 44. Resistance 66 in the infusion system may change over time and the resistance determination may be updated. The compliance 68 is preferably stored in memory at 34 to be accessible to the scaler 64.

Scaling 64 by the fluid flow resistance 66 and the compliance 68 of the compliant chamber 44 results in a value which may be referred to as the differential pressure ($P_{diff}$), to which the equilibrium pressure is added in the adder 70 to determine head pressure. The value of the head pressure is compared in comparator 72 to a first threshold reference value 74 to determine whether the fluid source pressure has fallen below a specified minimum and thereby indicating an empty fluid supply. The head pressure value is compared in comparator 72 to a second threshold reference value 76 to determine if the head pressure is so low as to indicate that an upstream occlusion exists.

The comparator 72 may also be programmed to monitor the change between measurements of head pressure and if the head pressure were to begin to change rapidly, such change may be taken to indicate that the fluid level is down in the neck of the supply bottle or the narrow part of the drip chamber or in the tubing itself in the case where the supply has a greater cross-sectional area than the tubing. Therefore, the difference between successive $P_{head}$ pressures is compared to a third threshold 78 to determine if such a condition exists. Monitoring the flow rate 79 to consider its effect on head pressure change can be used in determining the existence of an empty fluid supply container. For example, if the flow rate remained steady while the change in head pressure increased, an empty fluid supply container could be indicated.

In an alternative embodiment, the downstream pressure measurements may be provided to the comparator 72 along line 82 and directly compared in the comparator 72 with a fourth threshold 80 for determining a gross variance with a predetermined minimum, to also detect an upstream occlusion of the fluid line.

Comparator 72 is adapted to generate an alarm signal 82 when the pressure values fall below the threshold values or the change in pressure exceeds a threshold.

The alarm signal 82 is received by an alarm generator 86 for generating an audio and/or visual or other type of alarm signal. Different alarm signals from the comparator 72 may result in different alarms. For example, an occlusion alarm may be a continuous tone while a low head pressure alarm may be a repeating tone. The display 40 displays the head pressure and the alarms as desired and may display other system information. Additionally, the microprocessor 26 may stop pump operation automatically upon issuance of an alarm signal by the alarm generator.

Other implementations of the integrator may include the use of electronic analog integration, hydraulic integration, or mechanical integration. Other methods which can evaluate the integral of a pressure wave can be used to implement this technique. Additionally, other types of pumps may also be used if the pump accommodates a compliant chamber capable of storing fluid at one of the pressures and subsequently connecting the chamber to the portion of the fluid line at the other pressure.

Referring again to FIG. 1, an embodiment is shown in which a float valve 88 is included with the drip chamber so that when the level of fluid in the drip chamber drops below a minimum level, the float valve 88 will occlude the upstream line 16. Continued operation of the pump 20 will produce the large negative pressure in the compliant chamber 44 as mentioned above and the large negative equalization pulse. Thus, the empty supply condition will be siganlled through the occlusion alarm. Other similar mechanisms which will not pass air, such as hydrophilic filter, may also be utilized in forcing an occlusion situation when the fluid source becomes empty.

In view of the foregoing, it can be appreciated that the apparatus and method for detecting upstream conditions in the intravenous fluid line in an intravascular fluid administration system provide such detection without the necessity of modifying an existing peristaltic pump mechanism. In the case where a downstream pressure transducer has already been installed, the signal processing can be modified in accordance with the invention to provide such upstream condition detection. The apparatus and method for detecting conditions in an intravenous fluid line in an intravascular fluid administration system provide a simple, low cost way of monitoring upstream occlusion without the necessity of modification of existing peristaltic pump mechanism. Placed in a downstream configuration, the system of the invention can be readily adapted to monitor upstream occlusion in existing peristaltic pump IV infusion systems.

Additionally, where the height 90 of the fluid supply above the compliant chamber is known as well as the inner diameter 90 of the upstream tubing and the cross-sectional area 90 of the fluid supply container, the amount of fluid remaining in the fluid supply could be determined from head pressure. Where the flow rate 79 through the pump of the fluid in the tubing is known, the amount of time remaining before the fluid supply is depleted can also be determined.

Although preferred and alternative embodiments of the invention have been described and illustrated, it is clear that the invention is susceptible to numerous modifications and adaptations within the ability of those skilled in the art and without the exercise of inventive faculty. Thus, it should be understood that various changes in form, detail and usage of the present invention may be made without departing from the spirit and scope of the invention.

What is claimed is:

1. A fluid line condition detection apparatus coupled between a fluid supply and a fluid receiver, the apparatus comprising:
   a fluid line having an upstream segment coupled to the fluid supply for receiving fluid from the fluid supply at head pressure and a downstream segment coupled to the fluid receiver;
   a fluid chamber disposed in fluid communication with the upstream segment and with the downstream segment of the fluid line;
   control means for alternately opening the fluid chamber to fluid communication with the upstream segment of the fluid line and with the downstream segment of the fluid line, wherein when opened to the upstream segment, the chamber receives and stores fluid at head pressure and wherein when opened to the downstream segment, the chamber communicates the fluid stored at head pressure to fluid residing in the downstream segment thereby causing a pressure equalization pulse in the downstream segment;
   pressure sensor means for sensing equilibrium pressure in the downstream segment and for providing an equilibrium signal representative thereof and for also sensing the pressure equalization pulse and for providing an equalization signal representative of the pressure equalization pulse; and
   processor means responsive to said equilibrium signal and to said equalization signal for taking the difference between the equilibrium signal and the equalization signal and for integrating the difference in determining the head pressure.

2. The apparatus of claim 1 further comprising:
   resistance means for providing a resistance signal representative of the resistance to fluid flow downstream of the fluid chamber;
   wherein the processor means is also for scaling the integrated difference by the resistance signal in determining head pressure.

3. The apparatus of claim 1 wherein:
   the fluid chamber has compliance;
   the apparatus further comprising compliance means for providing a compliance signal representative of the compliance of the fluid chamber; and
   wherein the processor is also for scaling the integrated difference by the compliance signal in determining head pressure.

4. The apparatus of claim 1 wherein the processor is also for scaling the integrated difference and adding the scaled, integrated difference to the equilibrium signal in determining head pressure.

5. The apparatus of claim 1 wherein:
the processor means is also for providing a head pressure signal representative of the determined head pressure; and
the apparatus further comprising an alarm generator which receives the head pressure signal, compares the received signal to a first threshold and if the head pressure signal is less than the first threshold, provides an occlusion alarm signal.

6. The apparatus of claim 1 wherein:
the processor means is also for providing a head pressure signal representative of the determined head pressure; and
the apparatus further comprising an alarm generator which receives the head pressure signal, compares the received signal to a second threshold and if the head pressure signal is less than the second threshold, provides an alarm signal indicating that the fluid supply is empty.

7. The apparatus of claim 1 wherein:
the processor means is also for comparing head pressures determined at different times to each other and for providing a head pressure difference signal representative of the difference between compared head pressures; and
the apparatus further comprising an alarm generator which receives the head pressure difference signal, compares said difference signal to a third threshold and if said difference signal exceeds the third threshold, provides an alarm signal indicating that the fluid supply is empty.

8. The apparatus of claim 7 further comprising:
flow rate means for sensing the flow rate of the fluid and providing a flow rate signal representative of the sensed flow rate;
wherein the processor means is also for receiving the flow rate signal and for comparing the change in the flow rate from the flow rate signal to the change in head pressure to determine the head pressure difference signal.

9. The apparatus of claim 1 wherein the processor means is also for receiving the size of the fluid line, the size of the fluid supply and the height of the fluid supply and based on head pressure, said sizes and height, determining the quantity of fluid remaining in the fluid supply.

10. The apparatus of claim 9 further comprising:
flow rate means for sensing the flow rate of the fluid and providing a flow rate signal representative of the sensed flow rate;
wherein the processor means is also for receiving the flow rate signal and based on the received flow rate signal and the quantity remaining in the fluid supply, providing a time remaining signal indicative of the amount of time remaining before the fluid supply is empty.

11. The apparatus of claim 1 wherein:
the fluid chamber is formed of flexible tubing which is connected at one end with the upstream segment of the fluid line and at the other end with the downstream segment of the fluid line; and
the control means comprises a peristaltic pump having a plurality of peristaltic occluding means for sequentially occluding the fluid chamber.

12. The apparatus of claim 1 further comprising valve means for preventing the flow of air into the upstream segment of the fluid line when the fluid supply becomes empty.

13. The apparatus of claim 12 wherein said valve means comprises a float valve disposed in fluid communication with the upstream segment of the fluid line between the fluid supply and the fluid chamber.

14. A fluid line condition detection apparatus coupled between a fluid supply and the vascular system of a patient, the apparatus comprising:
a fluid line having an upstream segment coupled to the fluid supply for receiving fluid from the fluid supply at head pressure and a downstream segment coupled to the vascular system of the patient;
a fluid chamber comprising a flexible segment of the fluid line disposed between and in fluid communication with the upstream segment and with the downstream segment of the fluid line;
control means for operating on the flexible segment of the fluid chamber to control the pressure of the fluid in the fluid line and for alternately opening the fluid chamber to fluid communication with the upstream segment of the fluid line and with the downstream segment of the fluid line, wherein when opened to the upstream segment, the chamber receives and stores fluid at head pressure and wherein when opened to the downstream segment, the chamber communicates the fluid stored at head pressure to fluid residing in the downstream segment thereby causing a pressure equalization pulse in the downstream segment;
pressure sensor means for sensing the pressure equalization pulse and for providing an equalization signal representative of the pressure equalization pulse and for sensing equilibrium pressure in the downstream segment and for providing an equilibrium signal representative thereof;
resistance means for providing a resistance signal representative of the resistance to fluid flow downstream of the fluid chamber;
processor means for taking the difference between the equilibrium signal and the equalization signal, integrating said difference and scaling the integrated difference by the resistance signal in determining the head pressure, said processor means also for providing a head pressure signal representative of the determined head pressure; and
an alarm generator which receives the head pressure signal, compares the received signal to a first threshold and if the head pressure signal is less than the first threshold, provides an occlusion alarm signal.

15. The apparatus of claim 14 wherein:
the fluid chamber has compliance;
the apparatus further comprising compliance means for providing a compliance signal representative of the compliance of the fluid chamber; and
wherein the processor is also for scaling the integrated difference by the compliance signal in determining head pressure.

16. The apparatus of claim 15 wherein the processor means further comprises adder means for adding the scaled, integrated difference to said equilibrium signal in determining the head pressure.

17. The apparatus of claim 14 wherein the processor is also for adding the integrated difference to the equilibrium signal in determining head pressure.

18. The apparatus of claim 14 wherein the alarm generator compares the received signal to a second threshold and if the head pressure signal is less than the second threshold, provides an alarm signal indicating that the fluid supply is empty.

19. The apparatus of claim 14 wherein the processor means is also for comparing determined head pressures to each other and for providing a head pressure difference signal representative of the difference between compared head pressures; and the alarm generator receives the pressure difference signal, compares said difference signal to a third threshold and if said difference signal exceeds the third threshold, provides an alarm signal indicating that the fluid supply is empty.

20. The apparatus of claim 19 further comprising:

flow rate means for sensing the flow rate of the fluid and providing a flow rate signal representative of the sensed flow rate;

wherein the processor means is also for receiving the flow rate signal and for comparing the change in the flow rate to the change in head pressure to determine the head pressure difference signal.

21. The apparatus of claim 14 wherein the processor means is also for receiving the size of the fluid line, the size of the fluid supply and the height of the fluid supply and based on head pressure, said sizes and height, determining the quantity of fluid remaining in the fluid supply.

22. The apparatus of claim 21 further comprising:

flow rate means for sensing the flow rate of the fluid and providing a flow rate signal representative of the sensed flow rate;

wherein the processor means is also for receiving the flow rate signal and based on the received flow rate signal and the quantity remaining in the fluid supply, providing a time remaining signal indicative of the amount of time remaining before the fluid supply is empty.

23. The apparatus of claim 14 wherein the fluid pressure control means comprises a peristaltic pump having a plurality of peristaltic means for operating on the flexible segment of the tubing for sequentially occluding the flexible segment wherein said fluid line pumping segment comprises the fluid chamber.

24. The apparatus of claim 14 further comprising valve means for preventing the flow of air into the upstream segment of the fluid line when the fluid supply becomes empty.

25. A method for detecting the condition of a fluid delivery system which includes a fluid line having an upstream segment coupled to a fluid supply and a downstream segment coupled to a fluid receiver, the delivery system having a fluid pressure control means for operating on a flexible segment of the fluid line to control the pressure of the fluid in the fluid line, the fluid upstream of the fluid pressure control means being at head pressure, the method comprising the steps of:

storing fluid at the head pressure in a fluid chamber disposed in fluid communication with the upstream segment and with the downstream segment of the fluid line;

alternately opening the fluid chamber to fluid communication with the upstream segment of the fluid line and with the downstream segment of the fluid line, wherein when opened to the upstream segment, the chamber receives and stores fluid at head pressure and wherein when opened to the downstream segment, the chamber communicates the fluid stored at head pressure to fluid residing in the downstream segment thereby causing a pressure equalization pulse in the downstream segment;

sensing the equilibrium pressure in the downstream segment and providing an equilibrium signal representative thereof and also sensing the pressure equalization pulse and providing an equalization signal representative of the pressure equalization pulse; and processing the equalization signal to determine the head pressure including the steps of taking the difference between the equilibrium signal and the equalization signal and integrating the difference in determining the head pressure.

26. The method of claim 25:

further comprising the steps of determining the resistance to fluid flow downstream of the fluid chamber and providing a resistance signal representative of said resistance;

wherein the step of processing further comprises the step of scaling the integrated difference by the resistance signal in determining head pressure.

27. The method of claim 25:

further comprising the step of determining the compliance of the material forming the fluid chamber; and wherein the step of processing further comprises the step of scaling the integrated difference by the compliance in determining head pressure.

28. The method of claim 25 wherein the step of processing comprises the steps of scaling the integrated difference and adding the scaled, integrated difference to the equilibrium signal in determining head pressure.

29. The method claim 25:

wherein the step of processing further comprises providing a head pressure signal representative of the determined head pressure; and further comprising the step of comparing the head pressure signal to a first threshold and providing an occlusion alarm signal if the head pressure is less than the first threshold.

30. The method of claim 25:

wherein the step of processing further comprises providing a head pressure signal representative of the determined head pressure; and further comprising the step of comparing the head pressure signal to a second threshold and providing an empty supply alarm signal if the head pressure is less than the second threshold.

31. The method of claim 25:

wherein the processing step further comprises the steps of comparing determined head pressures to each other and providing a head pressure difference signal representative of the difference between compared head pressures; and further comprising the step of comparing said difference signal to a third threshold and providing an alarm signal indicating that the fluid supply is empty if said difference signal exceeds the third threshold.

32. The apparatus of claim 31 further comprising:

flow rate means for sensing the flow rate of the fluid and providing a flow rate signal representative of the sensed flow rate;

wherein the processor means is also for receiving the flow rate signal and for comparing the change in the flow rate to the change in head pressure to determine the head pressure difference signal.

33. The apparatus of claim 25 wherein the processor means is also for receiving the size of the fluid line, the size of the fluid supply and the height of the fluid supply and based on head pressure, said sizes and height, determining the quantity of fluid remaining in the fluid supply.

34. The apparatus of claim 33 further comprising:
flow rate means for sensing the flow rate of the fluid and providing a flow rate signal representative of the sensed flow rate;
wherein the processor means is also for receiving the flow rate signal and based on the received flow rate signal and the quantity remaining in the fluid supply, providing a time remaining signal indicative of the amount of time remaining before the fluid supply is empty.

35. The method of claim 25 further comprising the step of preventing the flow of air into the upstream segment of the fluid line when the fluid supply becomes empty.

* * * * *